US005480426A

United States Patent [19]
Chu

[11] Patent Number: 5,480,426
[45] Date of Patent: * Jan. 2, 1996

[54] METHOD OF IMPLANTING AN INTRAOCULAR LENS HAVING HAPTICS FOR SCLERAL FIXATION

[76] Inventor: Milton W. Chu, 5800 Santa Rosa Rd., Suite 111, Camarillo, Calif. 93012

[*] Notice: The portion of the term of this patent subsequent to Aug. 9, 2011, has been disclaimed.

[21] Appl. No.: 189,069

[22] Filed: Jan. 28, 1994

Related U.S. Application Data

[63] Continuation-in-part of Ser. No. 929,887, Aug. 22, 1992, Pat. No. 5,336,262, which is a continuation-in-part of Ser. No. 456,809, Dec. 26, 1989, abandoned.

[51] Int. Cl.⁶ .......................................................... A61F 2/16
[52] U.S. Cl. .................................................................. 623/6
[58] Field of Search ...................................................... 623/6

[56] References Cited

U.S. PATENT DOCUMENTS

| | | | |
|---|---|---|---|
| 4,041,552 | 8/1977 | Ganias | 623/6 |
| 4,304,012 | 12/1981 | Richard | 623/6 |
| 4,327,450 | 5/1982 | Girard | 623/6 |
| 4,409,690 | 10/1983 | Gess | 623/6 |
| 4,666,444 | 5/1987 | Pannu | 623/6 |
| 4,778,463 | 10/1988 | Hetland | 623/6 |

OTHER PUBLICATIONS

Physicians' Desk Reference for Ophthalmology (book), 14th Edition, 1986, Publisher: Edward R. Barnhart, pp. 169–170, Coburn Models 6Z and 62 UV 623–6.
IOPTEX, Control–Loop Haptic, Ultra C–Loop Model C304, Jun. 1983.
Bloomberg, Leroy, "Buried–Knot Fixation of a Single–Piece PCL", Sep. 1991, pp. 1–3.

*Primary Examiner*—Mary Beth O. Jones
*Attorney, Agent, or Firm*—Pretty, Schroeder, Brueggemann & Clark

[57] ABSTRACT

An intraocular lens suitable for scleral fixation is provided, having a disk-shaped lens optic with two flexible haptics projecting outwardly from opposite points on the lens optic's periphery, each haptic including one or more suture holes for use in suturing the haptic to the ciliary sulcus of an eye during implantation surgery. The suture holes are positioned such that they are located substantially at the haptic apexes when the lens is implanted and the haptics have been flexed inwardly a predetermined amount. In addition, the suture holes are sized to be in the range of 0.20 to 0.25 millimeters, which is large enough to receive standard sutures, but small enough to prevent excessive movement of the haptic relative to the suture and to inhibit tissue ingrowth and incarceration. This configuration minimizes the possibility of lens tilting, decentration and rotation.

6 Claims, 3 Drawing Sheets

METHOD OF IMPLANTING AN INTRAOCULAR LENS HAVING HAPTICS FOR SCLERAL FIXATION

CROSS-REFERENCE TO RELATED APPLICATION

This is a continuation-in-part of U.S. application Ser. No. 07/929,887, filed Aug. 22, 1992, and now U.S. Pat. No. 5,336,262 which is a continuation-in-part of U.S. application Ser. No. 07/456,809, filed Dec. 26, 1989, and now abandoned.

BACKGROUND OF THE INVENTION

1. Field of the Invention

This invention relates generally to intraocular lenses and, more particularly, to intraocular lenses having haptics adapted for scleral fixation.

2. Description of the Related Art

FIG. 1 is a cross-sectional view of a typical, healthy human eye 100. The human eye is a generally spherical body defined by an outer wall called the sclera 110, having a transparent bulbous front portion called the cornea 112. The lens 114 of the human eye is located within the spherical body, behind the cornea. The iris is located between the lens and the cornea, dividing the eye into an anterior chamber 120 in front of the iris and a posterior chamber 118 in back of the iris. A central opening in the iris, called the pupil 122, controls the amount of light that reaches the lens. Light is focused by the cornea and by the lens onto the retina at the rear of the eye. The lens is a bi-convex, highly transparent structure surrounded by a thin lens capsule 126. The lens capsule is supported at its periphery by suspensory ligaments called zonules 128, which are continuous with the ciliary muscle 130. The focal length of the lens is changed by the ciliary muscle. Just in front of the zonules, between the ciliary muscle and iris, is a region referred to as the ciliary sulcus 132.

A cataract condition results when the material of the lens 114 becomes clouded, thereby obstructing the passage of light. To correct this condition, three alternative forms of surgery are used, known as intracapsular extraction, extracapsular extraction, and phacoemulsification. In intracapsular cataract extraction, the zonules 128 around the entire periphery of the lens capsule are severed, and the entire lens structure, including the lens capsule 126, is then removed. In extracapsular cataract extraction and phacoemulsification, only the clouded material within the lens capsule is removed, while the transparent posterior lens capsule wall with its peripheral portion, as well as the zonules, are left in place in the eye.

Intracapsular extraction, extracapsular extraction, and phacoemulsification eliminate the light blockage due to the cataract condition. The light entering the eye, however, is thereafter unfocused due to the lack of a lens. A contact lens can be placed on the exterior surface of the eye, but this approach has the disadvantage that the patient has virtually no useful sight when the contact lens is removed. A preferred alternative is to implant an artificial lens, known as an intraocular lens, directly within the eye. An intraocular lens generally comprises a disk-shaped, transparent lens optic and two smoothly curved attachment arms referred to as haptics. The lens is implanted through an incision made near the periphery of the cornea, which may be the same incision as is used to remove the cataract. An intraocular lens may be implanted in either the anterior chamber of the eye, in front of the iris, or in the posterior chamber, behind the iris.

An anterior chamber lens is supported by contact of the haptics with a corner, or angle, of the anterior chamber 120 which is formed by the union of the iris 116 and the cornea 112. In the case of a posterior chamber lens, there are two alternative techniques of support. In the first technique, the intraocular lens and its haptics are placed in the sack-like structure formed by the intact posterior and peripheral walls of the lens capsule. The haptics are compressed slightly against the periphery of the lens capsule and thereby hold the intraocular lens in place. In the second technique, the intraocular lens is placed in front of and outside the lens capsule. The haptics are sandwiched between the iris 116 and the zonules 128, in the region of the ciliary sulcus 132, to hold the lens in place. Anterior chamber lenses differ significantly in design from posterior chamber lenses. Accordingly, one cannot be used in substitution for the other.

Experience has shown that intraocular lenses implanted in the anterior chamber dramatically increase the risk of significant complications. Anterior chamber lenses have been known to cause hyphema, uveitis, iris chaffing, glaucoma, cystoid macular edema, persistent ocular pain and redness, and pseudophakic bullous keratopathy. As a result of treating these conditions and other complications, anterior chamber lenses need to be explanted, or removed, approximately 20 times more often than posterior chamber lenses. For these reasons, when adequate zonular or capsular support is present, the posterior chamber lens generally remains the surgeon's first choice.

Unfortunately, adequate zonular or capsular support is not always present. Certain abnormalities of the eye, traumatic injury to the eye, previous intracapsular surgery, or an intra-operative complication during extracapsular or phacoemulsification surgery, all can result in a loss of the capsular or zonular support for a posterior chamber lens. Until recently, the surgeon has had no choice but to implant an anterior chamber lens.

However, surgeons have recently succeeded in implanting intraocular lenses in the posterior chamber in the absence of capsular and zonular support by suturing the lens to the sclera of the eye. The lens haptics are usually sutured to the sclera at or near the ciliary sulcus. The limited number of surgeons who have experimented with scleral fixation have reported promising results. Early reports show that intraocular lenses attached to the eye by scleral fixation are well tolerated, provide good vision, and bear significantly fewer complications than anterior chamber lenses. If these promising results continue to be confirmed, scleral-fixated posterior chamber lenses could make anterior chamber lenses obsolete.

Standing in the way of rapid adoption of scleral fixation for posterior chamber lenses is the fact that specialized lenses and materials to perform the procedure are not yet available. Most ophthalmic surgeons can easily acquire the surgical skills needed for scleral fixation. Suitable sutures and needles are presently available for the procedure, such as the 10-prolene suture and the Ethicon CIF-4 or STC-6 needles. However, intraocular lens designed specifically for scleral fixation are not widely known or available.

At present, ophthalmic surgeons ordinarily use conventional posterior chamber lenses and simply tie the fixation sutures to the lens haptics. There are several drawbacks to this technique. First, because the fixation suture is tied to the smooth haptic, migration of the haptic and lens optic relative to the suture is possible. Such migration could lead to lens decentration, lens tilt, or even complete loss of lens fixation. Second, the process of tying the suture to the lens haptic (generally with a double knot or a clove hitch) is a difficult, time consuming, and often frustrating procedure. If the suture is tied to the haptic with a double knot, the end of the suture may irritate the inside of the eye. These problems are amplified by the need to repeat the procedure for each haptic. Third, current posterior chamber lenses are considered too large for scleral-fixated placement in the typical posterior chamber. The diameter of the typical ciliary sulcus measures about 11 millimeters, while the typical posterior chamber lens measures 14 millimeters across. Finally, the haptics of current posterior chamber lenses do not provide optimal stability of the lens optic in the absence of the lens capsule. Such instability can lead to lens tilting and can introduce uncorrectable optical problems after scleral fixation.

Some ophthalmic surgeons have experimented with sclerally fixating lenses of the kind that include instrument positioning holes at various positions along their haptics. These holes have sizes typically of 0.50 millimeters, but are known to have sizes as low as 0.34 millimeters. The use of this type of lens has not proven to be entirely satisfactory, because the implanted lenses are believed to have been subject to excessive tilting, decentration and rotation. In addition, the instrument positioning holes of such implanted lenses are subject to tissue ingrowth and incarceration, which can lead to lens decentration and can make later removal or repositioning of the lenses difficult or impossible to perform.

It should therefore be appreciated that there is a need for an intraocular lens, and a method for implanting it in the eye by scleral fixation, which is convenient to implant and which is sufficiently stable when implanted that it minimizes the possibility of tilting or decentering. The present invention fulfills this need.

SUMMARY OF THE INVENTION

The present invention is embodied in an intraocular lens, and related method for implanting it in an eye, in which the lens is specially configured for sclera fixation, is convenient to implant, and is sufficiently stable when implanted that it minimizes the possibility of tilting or decentering. More particularly, the intraocular lens includes a disk-shaped lens optic with first and second curved, position-fixation haptics projecting outwardly from opposite points on the lens optic's periphery. Each haptic projects outwardly from, and then back inwardly toward, the lens optic so as to define an apex. In addition, each haptic includes one or more suture holes sized to receive a suture for attaching the haptic to the surface of the eye's sclera. To maximize the len's stability, the suture holes are positioned on the haptics such that they lie substantially at the haptic apexes when the lens is implanted in the eye.

When implanted, the haptics are flexed inwardly to engage the ciliary sulcus, which ordinarily has a diameter of about 11 millimeters. To ensure that the suture holes are located at the haptic apexes when the lens is installed, they are located a predetermined distance short of the apexes when the haptics are unflexed, prior to implantation. After implantation, the center of the suture holes are preferably located within the first 1.5 millimeters of tangential contact with the ciliary sulcus. Further, the lens can be provided in a smaller transverse size, approximately 12.5 millimeters, which is better suited for the dimensions of the ciliary sulcus as compared with the 14-millimeter size of typical posterior chamber lenses.

In another feature of the invention, each suture hole is sized significantly smaller than typical instrument positioning holes of conventional lenses. A circular suture hole having a diameter of 0.25 millimeters or less, and preferably 0.20 to 0.25 millimeters, significantly reduces undesired movement of the suture along the haptic and thereby provides an implanted lens that is stable and highly resistant to tilting, decentration and rotation. In addition, the smaller hole size substantially reduces undesired tissue ingrowth and incarceration.

In another feature of the invention, the axial/radial orientation of the suture holes can be selected to minimize torsional forces arising between the suture and the haptic. Preferably, each suture hole is oriented in a direction toward the ciliary sulcus. The suture is thereby guided in the most direct route possible to the point of scleral fixation by the suture hole. This eliminates the problem of torsional forces on the haptic that can be generated by interaction between the suture and the haptic. Such torsional forces can bow the lens out and can lead to lens decentration or tilting.

In addition, the lens of the invention eliminates the necessity of maintaining an inventory of anterior chamber lenses, because the present invention provides an intraocular lens that can be implanted in the posterior chamber of the eye even in the absence of capsular support. Further, a lens in accordance with the present invention can alternatively be used in the posterior chamber without scleral fixation but with conventional capsular or zonular support.

Other features and advantages of the present invention should become apparent from the following description of the preferred embodiments, taken in conjunction with the accompanying drawings, which illustrate, by way of example, the principles of the invention.

DESCRIPTION OF THE PREFERRED EMBODIMENTS

The following description of the invention is not to be taken in a limiting sense but is made merely for the purpose of illustrating the general principles of the invention. The scope of the invention is best defined by the appended claims. The following detailed descriptions describes the best presently contemplated modes of carrying out the present invention.

Figure 2:
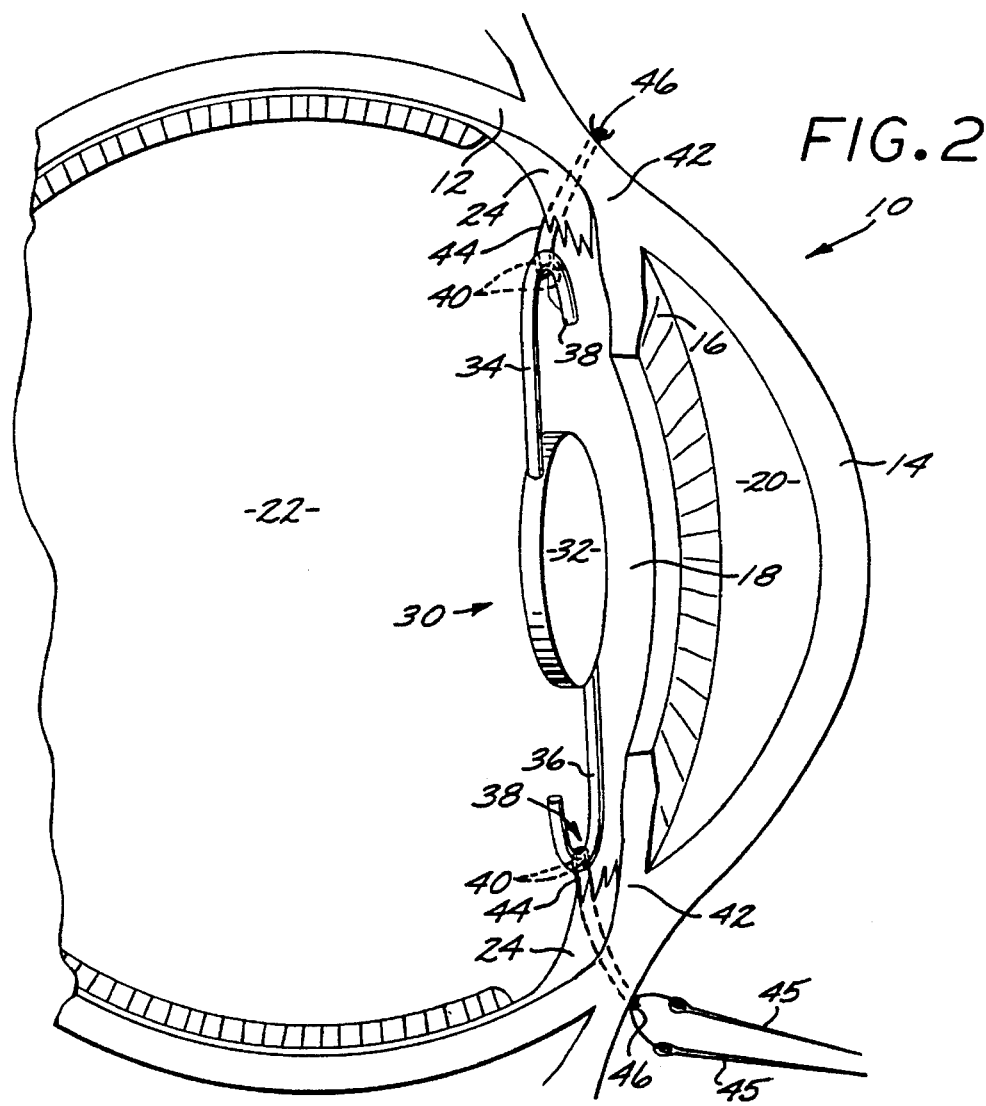
FIG. 2 is a cross-sectional, perspective view of an intraocular lens in accordance with the present invention, implanted in an eye.

FIG. 2 shows a first embodiment of an intraocular lens 30 in accordance with the present invention, as implanted within the posterior chamber of an eye 10. The spherical body of the eye is defined by the sclera 12, with the eye's forward end being a transparent, bulbous segment referred to as the cornea 14. An iris 16 extends radially inwardly at the juncture of the sclera and the cornea. The iris is a pigmented, ring-shaped mass of tissue that controls the amount of light passing to the lens. The central opening in the iris is referred to as the pupil 18. The iris divides the eye into a front or anterior chamber 20 and a rear or posterior chamber 22. A ciliary muscle 24 is located around the inside of the eye, behind the iris, with suspensory ligaments called zonules ordinarily extending from the ciliary muscle radially inward to a lens capsule that supports the lens of the eye. In FIG. 2, the lens, lens capsule, and zonules have been surgically removed.

Figure 3:
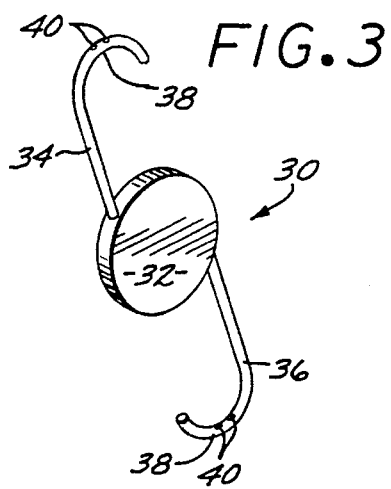
FIG. 3 is a perspective view of the intraocular lens illustrated in FIG. 2.

The intraocular lens 30 in accordance with the present invention is shown in FIG. 2 implanted in the eye 10 within the posterior chamber 22, while the lens is shown by itself in perspective in FIG. 3. The lens 30 includes a disk-shaped lens optic 32 and curved first and second haptics 34 and 36, respectively, attached to the lens optic at opposite points on the lens optic's periphery. The haptics lie substantially in the transverse plane of the lens optic, and they each project outwardly from, and then back inwardly toward, the lens optic, so as to define an apex 38.

Each haptic 34 or 36 includes a pair of radially-oriented suture holes 40 directed toward the ciliary sulcus 42, just anterior to the ciliary muscle 16. A suture 44 is threaded through a first of the suture holes in one direction and through the other suture hole in the opposite direction, and each free end of the suture is passed through the sclera 12 using a needle 45. The free ends are then secured together in a knot 46. When the suture is passed through the suture holes 40, the suture is held in a fixed position relative to the haptic, and thus there can be no migration of the haptic and lens optic. The suture holes, being radially directed toward the ciliary sulcus, guide the needle and suture in the most direct route possible to the point of scleral fixation. Because two suture holes are provided, there is no need to fasten the suture to the haptic with a knot, which eliminates one potential cause of irritation to the sclera. In the embodiment illustrated, only smooth surfaces are located at the point of fixation.

The suture holes 40 are sized to be large enough to allow the passage of standard sutures (typically about 28 microns), but small enough to prevent excessive movement of the haptic 34 or 36 relative to the suture 44 and further small enough to prevent tissue ingrowth and incarceration. A circular cross-section of diameter between about 0.20 and 0.25 millimeters is preferred. This size is substantially smaller than the typical size of instrument positioning holes used in the past for mechanically positioning the haptic during the implantation procedure. Avoiding movement of the haptic relative to the suture and further avoiding tissue ingrowth and incarceration by means of smaller-sized holes is desirable because those occurrences can lead to unwanted lens tilting, decentration and rotation. Tissue ingrowth also can make later removal or repositioning of the lens difficult or impossible to perform.

Another advantage of using such small-diameter suture holes is that the suture can be secured in place by merely knotting it at its end rather than wrapping around the haptic or threading through an adjacent suture hole. The knotted end of the suture is too large to pass through the suture hole.

The ciliary sulcus 42 typically has a diameter of about 11 millimeters. The lens 30 therefore preferably has an overall length of only about 12.5 millimeters, which is significantly smaller than the 14.0 millimeter length of the typical posterior chamber lens. This latter length is considered too large for effective use as a sclerally-fixated lens. When implanted, the haptics 34 and 36 therefore each flex inwardly by about 0.5 to 1.0 millimeters. It will be appreciated, therefore, that in the case of open-loop haptics like these, a different portion of each haptic will form the apex after implantation as compared to before implantation. It is desirable for the suture holes to be positioned at the haptic apex when the lens is implanted, to maximize the implanted lens' stability, so the holes desirably are positioned somewhat short of the apex when the haptic is in an unflexed state.

Figure 4:
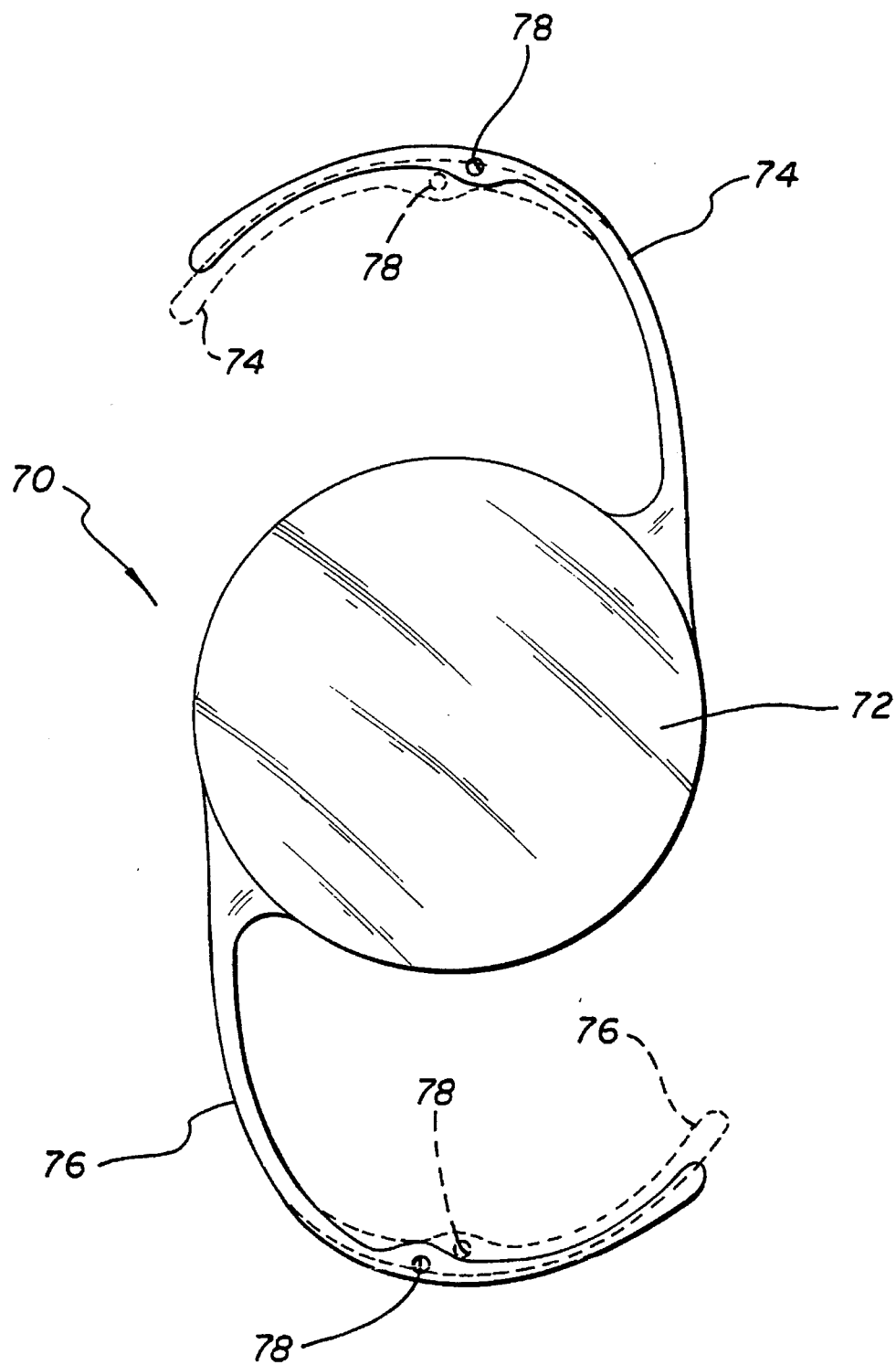
FIG. 4 is a plan view of a second intraocular lens embodiment of the present invention, with dotted lines indicating the inwardly-flexed positions of the haptics after implantation.

This will be better understood with reference to FIG. 4, which discloses a second embodiment of an intraocular lens 70 in accordance with the invention. This lens includes a disk-shaped lens optic 72 with open-loop haptics 74 and 76. A single suture hole 78 is provided in each haptic. When the haptics are in their unflexed state, represented by the solid lines in FIG. 4, the suture holes 78 are located slightly short of the haptics' apexes. However, when the haptics are flexed inwardly by an amount corresponding to the amount of flex that occurs when implanted, represented by dotted lines in FIG. 4, the suture holes are located substantially at the haptics' apexes.

Figure 1:
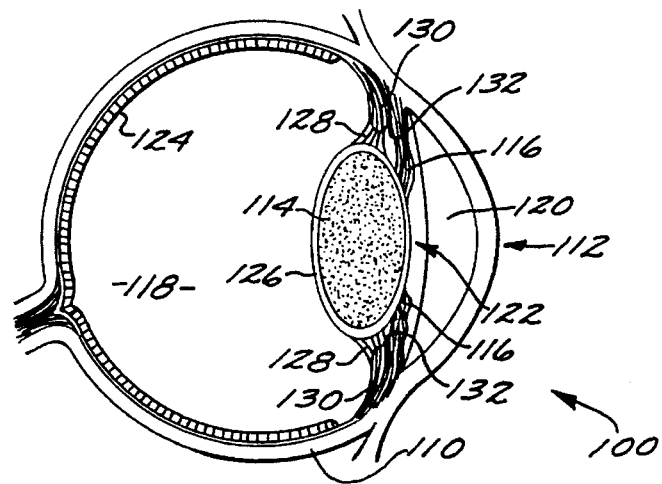
FIG. 1 is a cross-sectional view of a typical healthy human eye.

It will be appreciated that, after implantation, the haptics 74 and 76 will both engage the ciliary sulcus 42 (FIGS. 1 and 2) for substantial distances along their lengths. The suture holes 78 preferably are positioned on the haptics such that the centers of the holes are located within the first 1.50 millimeters of tangential contact with the ciliary sulcus.

Figure 5:
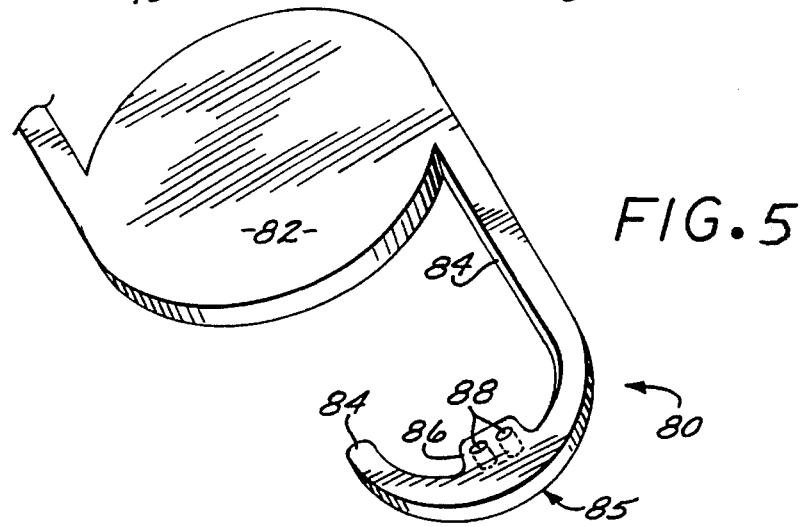
FIG. 5 is a perspective view of a portion of a third intraocular lens embodiment of the present invention, with phantom lines indicating axially-aligned suture holes in tabs secured to one of its haptics.

FIG. 5 is an enlarged perspective view of a third embodiment of the present invention. An intraocular lens 80 is shown having a disk-shaped lens optic 82 with an open loop haptic 84 (only one haptic of a pair is shown). At its apex portion 85, the haptic includes a disk-shaped tab 86. Several methods of creating the tab can be used. The tab can be punch-cut from the material used to form the haptic, thereby becoming an integral part of the haptic when it is being formed, or alternatively the tab can be separately formed and then attached to the haptic, for example, by localized heating that fuses the tab to the haptic, or by chemical bonding. The tab could also be integrally formed by pinching or flattening the apex portion 85 when the haptic has been formed and is still somewhat soft and pliable. The tab includes two suture holes 88 extending axially through it, i.e., in a direction substantially perpendicular to the transverse plane of the lens optic. When a suture is passed through the suture holes, the suture is held in a fixed position relative to the haptic. Because there are two suture holes, the suture can be attached to the haptic without a knot. Once again, only smooth surfaces are presented at the point of fixation.

Figure 6:
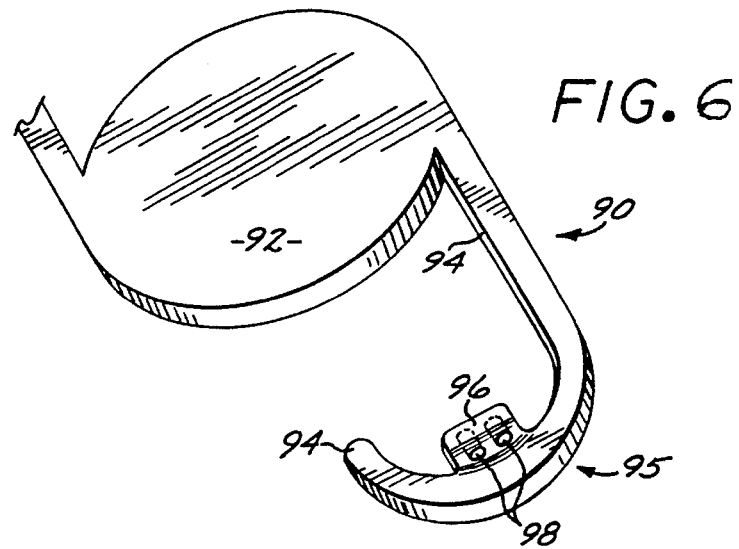
FIG. 6 is a perspective view of a portion of a fourth intraocular lens embodiment of the present invention, with phantom lines indicating radially-aligned suture holes in tabs secured to one of its haptics.

FIG. 6 is an enlarged perspective view of a fourth embodiment of the present invention. Like the embodiment of FIG. 5, the intraocular lens 90 has a disk-shaped lens optic 92 and a pair of open-loop haptics 94 (only one of which is illustrated), with an apex portion 95 of each haptic having a tab 96. In the FIG. 6 embodiment, each tab includes a pair of suture holes 98 extending radially through the tab, i.e., in a direction substantially parallel to the transverse plane of the lens optic. The suture holes in the tab are clear of the narrow part of the haptic, and a suture and needle may be passed through the suture holes for scleral fixation of the lens 90 to the eye. Again, the tab can be formed as an integral part of the haptic or can be separately formed and attached to the haptic, for example, by heat fusing or chemical bonding. The suture holes 98 are directed transversely to guide the suture and needle in the most direct route to the ciliary sulcus and the point of scleral fixation. When a suture is passed through the suture holes, the suture is held in a fixed position relative to the haptic. Only smooth surfaces are presented at the point of fixation.

Figure 7:
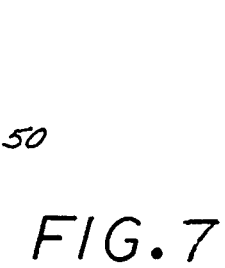
FIG. 7 is a plan view of a fifth intraocular lens embodiment of the present invention, with phantom lines indicating suture holes in its haptics.

FIG. 7 shows yet another embodiment of an intraocular lens in accordance with the present invention. The lens 50 includes a disk-shaped lens optic 52 and two closed loop haptics 54 and 56 oriented generally in the plane of the lens optic. The haptic 54 is attached to the lens optic at points 58 and 60, and the other haptic 56 is attached to the lens optic at points 62 and 64. The apex 66 of each closed loop haptic includes two suture holes 68 extending radially outwardly through the haptic, in the transverse plane of the lens optic 52. The lens of FIG. 7 may be attached in the posterior chamber of the eye in the same manner as that illustrated in FIG. 2. In particular, a needle and suture are passed through the suture holes 68 and are then guided by the holes to the sclera. The closed loop haptic design can sometimes provide better stability against tilting of the lens optic and resists decentration better than conventional open-loop haptic designs for posterior chamber lenses, and the lens sometimes can be made with a smaller overall length, to fit more easily in the ciliary sulcus. In addition, the closed-loop haptic design eliminates the free ends of the haptics that could potentially be a source of eye irritation or intraocular trauma.

The present invention has been described above in terms of several presently preferred embodiments so that an understanding of the present invention can be conveyed. There are, however, many configurations for lenses not specifically described herein, but to which the present invention applies. The present invention should therefore not been seen as limited to the particular embodiments described herein, but rather, it should be understood that the present invention has wide applicability with respect to lenses and haptics. Such other configurations may be achieved by those skilled in the art in view of the descriptions herein.

I claim:

1. A method of implanting an intraocular lens in the posterior chamber of an eye, comprising the steps of:

providing an intraocular lens having a disk-shaped lens optic with a transverse plane and first and second curved, flexible haptics projecting outwardly from opposite points on the lens optic's periphery, wherein the haptics each project outwardly from, and then back inwardly toward, the lens optic so as to define an apex, and wherein the haptics each include one or more suture holes; and implanting the lens in the posterior chamber of the eye, the step of implanting including steps of flexing the first and second haptics radially inwardly a combined distance of at least about 1 millimeter, such that they engage the ciliary sulcus of the eye, and passing a suture through the one or more suture holes of each of the first and second haptics and through the sclera of the eye, to secure the haptics, and thereby the lens, in place;

wherein the step of providing includes a step of locating the one or more suture holes in each of the first and second haptics such that when the lens is implanted in the eye, at least one suture hole in each haptic is located substantially at the haptic's apex, with the center of the suture hole within the first 1.5 millimeters of tangential contact with the ciliary sulcus.

2. A method as defined in claim 1, wherein the step of providing includes a step of providing haptics that have apexes that are approximately 12.5 millimeters apart from each other before the lens is implanted in the eye and further includes a step of locating the one or more suture holes in each of the first and second haptics such that, when the lens is implanted in the eye, at least one suture hole in each haptic is located substantially at the apex of each haptic when the haptics are flexed radially inwardly by the ciliary sulcus to points where the apexes are approximately 11 millimeters apart from each other.

3. A method as defined in claim 1, wherein the step of providing includes a step of providing only one suture hole on each haptic.

4. A method as defined in claim 1, wherein the step of providing includes a step of providing suture holes having a circular cross-section with a diameter between 0.15 and 0.25 millimeters.

5. A method as defined in claim 1, wherein the step of flexing the first and second haptics includes a step of flexing each haptic radially inwardly at least 0.5 millimeters.

6. A method as defined in claim 5, wherein the step of flexing the first and second haptics includes flexing each haptic radially inwardly less than 1.0 millimeters.

\* \* \* \* \*